(12) United States Patent
Hoshi et al.

(10) Patent No.: US 6,562,357 B2
(45) Date of Patent: *May 13, 2003

(54) BLACKHEAD REMOVING SHEET AND METHOD FOR PRODUCING BLACKHEAD REMOVING SHEET

(75) Inventors: Masaru Hoshi, Kanagawa-ken (JP); Hideaki Okabe, Kanagawa-ken (JP)

(73) Assignee: Lintec Corporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/327,031

(22) Filed: Jun. 7, 1999

(65) Prior Publication Data

US 2002/0022011 A1 Feb. 21, 2002

(30) Foreign Application Priority Data

Jun. 10, 1998 (JP) .............................. 10-178146
Jun. 10, 1998 (JP) .......................... 10-178147

(51) Int. Cl.[7] .................. A01N 25/34; A61F 13/00; A61K 31/74; A61K 31/85
(52) U.S. Cl. .................. 424/402; 424/443; 424/400; 424/449; 424/78.02; 424/78.08; 424/78.23
(58) Field of Search .................. 424/78.03, 401, 424/402, 448

(56) References Cited

U.S. PATENT DOCUMENTS

| 3,598,123 A | | 8/1971 | Zaffaroni | |
|---|---|---|---|---|
| 4,880,416 A | * | 11/1989 | Horiuchi et al. | 604/307 |
| 5,338,490 A | | 8/1994 | Dietz et al. | |
| 5,362,420 A | | 11/1994 | Itoh et al. | |
| 5,389,376 A | | 2/1995 | Duan et al. | |
| 5,512,277 A | * | 4/1996 | Uemura et al. | 424/78.03 |
| 5,968,537 A | * | 10/1999 | Crotty et al. | |
| 5,993,838 A | * | 11/1999 | Croty et al. | 424/402 |
| 6,106,818 A | * | 8/2000 | Dulog et al. | 424/78.03 |
| 6,190,683 B1 | * | 2/2001 | Hoshi et al. | |

FOREIGN PATENT DOCUMENTS

| DE | 199 11 262 A | | 9/2000 |
|---|---|---|---|
| EP | WO 97/32567 | * | 9/1997 |
| JP | 04-54107 | | 2/1992 |
| JP | 04-54108 | | 2/1992 |
| JP | 3046929 | | 3/1998 |
| WO | WO 98/48858 | | 11/1998 |
| WO | WO 99/38473 | | 8/1999 |

* cited by examiner

Primary Examiner—Thurman K. Page
Assistant Examiner—Isis Ghali
(74) Attorney, Agent, or Firm—Brinks Hofer Gilson & Lione; G. Peter Nichols

(57) ABSTRACT

A blackhead removing agent, a blackhead removing sheet and a method for producing the blackhead removing sheet are disclosed. The blackhead removing sheet comprises a base layer which is composed of a nonwoven fabric having the fineness of 0.0001 denier or more but less than 0.1 denier, and a blackhead removing layer consisting of the blackhead removing agent that contains a water-soluble macromolecular compound as a primary component. The blackhead removing agent comprises a water-soluble macromolecular compound, a filler, and a plasticizer that is compatible with the water-soluble macromolecular compound. The amount of the plasticizer in the blackhead removing agent is less than 0.01 parts by weight with respect to 100 parts by weight of the water-soluble macromolecular compound. The water-soluble macromolecular compound preferably includes a copolymer of N-vinyl-2-pyrrolidone and vinyl acetate as a primary component.

16 Claims, 2 Drawing Sheets

BLACKHEAD REMOVING SHEET AND METHOD FOR PRODUCING BLACKHEAD REMOVING SHEET

BACKGROUND OF THE INVENTION

1. Field of the Invention

The present invention relates to a blackhead removing agent for removing blackheads which include keratin, sebum, dirt or the like clogging the pores of the skin. The present invention also relates to a blackhead removing sheet, and to a method for producing such a blackhead removing sheet.

2. Description of the Prior Art

Peel-off types of blackhead removing agents and sheet types of blackhead removing agents have recently been proposed for removing blackheads or dirt in pores.

First, the prior art relating to peel-off types of blackhead removing agents will be described.

Peel-off types of blackhead removing agents are used in the following manner. A liquid blackhead removing agent is first applied by hand onto the face or the like. The applied blackhead removing agent is then left alone to dry. Thereafter, the dried blackhead removing agent is peeled off.

However, a problem with such peel-off types of blackhead removing agents is that the fingers become soiled by the blackhead removing agent when it is applied. Another problem is that it is relatively difficult to evenly apply the blackhead removing agent on the face. Yet another problem is that it takes a long time to allow the applied blackhead removing agent to dry. Still another problem is that part of the blackhead removing agent tends to remain on the skin when the dried blackhead removing agent is peeled off of the face.

Sheet types of blackhead removing agents (blackhead removing sheets) have thus been proposed to remedy the problems related to the aforementioned conventional peel-off types of blackhead removing agents, and to make it easier to remove blackheads. Such blackhead removing sheets comprise a layer composed of a base material (base material layer) and a layer composed of a blackhead removing agent (blackhead removing layer), which are laminated together.

Next, the prior art related to sheet types of blackhead removing agents is described below.

One example of sheet types of blackhead removing agents (blackhead removing sheet) has been disclosed in Japanese Laid-open Patent Application (Kokai) 10-77212. A liquid plasticizer that is compatible with the water-soluble macromolecular compound serving as a primary component and that imparts plasticity is added to the blackhead removing agent of this blackhead removing sheet in order to keep the blackhead removing layer from becoming too hard. Glycerin, 1,3-butanediol, and the like have been used as plasticizers. When such a plasticizer is added to the blackhead removing agent, the blackhead removing layer can be effectively prevented from becoming too hard.

However, such blackhead removing sheets suffer from the following problems.

One problem with conventional blackhead removing sheets is the insufficient strength of the blackhead removing layer after it has dried.

High adhesive strength for blackheads cannot be obtained in the aforementioned blackhead removing sheet since the blackhead removing agent has been plasticized by the addition of a plasticizer. Thus, a problem with such conventional blackhead removing sheets is that blackheads cannot be sufficiently removed.

Further in general, hydrophilic plasticizers exhibit poor volatility or nonvolatility from room temperature to around body temperature. Therefore, in the case of conventional blackhead removing sheets, the blackhead removing sheet must be left for long periods of time to allow the blackhead removing layer to dry. It is thus inconvenient for a user to leave the blackhead removing sheet on for long periods of time.

Next, problems involved in the use of woven fabrics and the like as the material for the base layer of such blackhead removing sheets are described below.

The blackhead removing layer of blackhead removing sheets must be kept moist when the blackhead removing sheet is used. In other words, the blackhead removing layer of the blackhead removing sheet must contain water when the blackhead removing sheet is used.

However, the blackhead removing layer is softened by moisture when the blackhead removing layer of the blackhead removing sheet contains water. The blackhead removing agent of the softened blackhead removing layer penetrates deeply into the gaps between the fibers in woven fabrics. As a result, the blackhead removing layer of the blackhead removing sheet can no longer adequately adhere to the skin. In other words, the blackhead removing layer can no longer adequately adhere to blackheads. Therefore, involve a problem in the blackhead removing capabilities are the conventional blackhead removing sheets.

In addition, the blackhead removing agent of the softened blackhead removing layer penetrates deeply into the gaps between the fibers of woven fabrics, so that the blackhead removing agent exudes from the outer surface of the base layer. A resulting problem is that the blackhead removing agent which is exuded from the outer surface of the base layer sticks to the fingers when the blackhead removing sheet applies to the skin, for example.

The use of a thick base layer as the base layer for blackhead removing sheets has been attempted as a means for remedying such problems involved in the conventional blackhead removing sheet described above. Such thick base layers do allow the blackhead removing agent to be prevented from exuding out of the surface of the base layer. On the other hand, however, there is a problem in that the base layer suffers a loss of flexibility. The blackhead removing sheets having such base layers that lack in flexibility involve problems in the conformability of the blackhead removing sheets with the skin, their adhesion to the skin, and their blackhead removing capabilities.

SUMMARY OF THE INVENTION

An object of the present invention is to provide a blackhead removing agent having excellent blackhead removing capabilities.

Another object of the present invention is to provide a blackhead removing agent that can be rapidly dried.

Still another object of the present invention is to provide a blackhead removing sheet having excellent conformability to the curved surface.

Yet another object of the present invention is to provide a method for producing a blackhead removing sheet having excellent conformability to the curved surface.

DETAILED DESCRIPTION OF THE PREFERRED EMBODIMENTS

Figure 1:
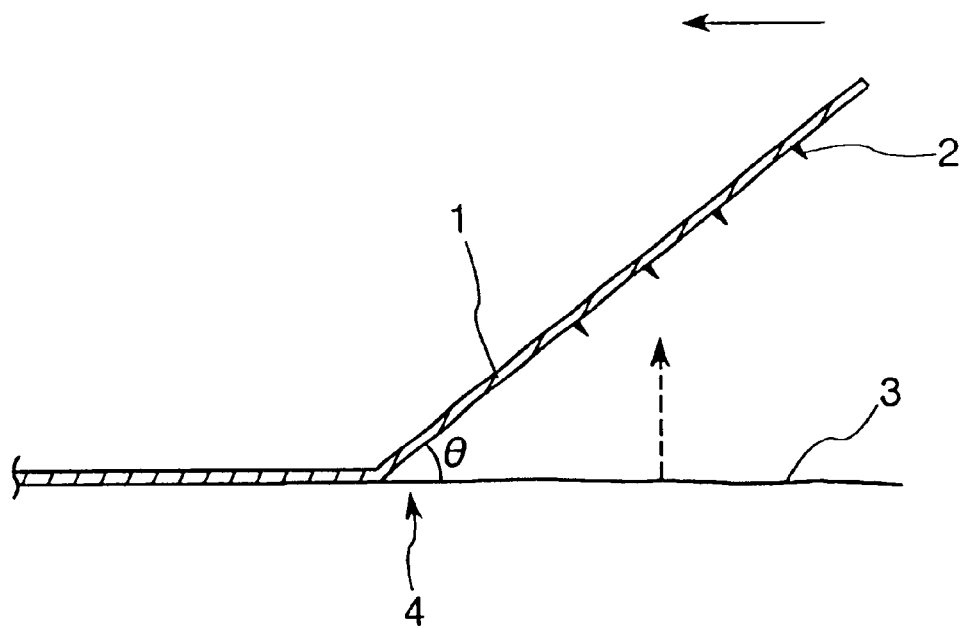
FIG. 1 shows the state that blackheads are peeled off from skin using a blackhead removing sheet of the present invention.

The blackhead removing agent, the blackhead removing sheet and the method for producing the blackhead removing sheet of the present invention are described in detail below based on preferred embodiments illustrated in the attached drawings.

The blackhead removing agent of the present invention comprises a water-soluble macromolecular compound and a filler. Further, the blackhead removing agent of the present invention contains virtually no plasticizer that is compatible with the water-soluble macromolecular compound. Specifically, the amount of the plasticizer in the blackhead removing agent of the present invention is less than 0.01 parts by weight with respect to 100 parts by weight of the water-soluble macromolecular compound.

According to this type of blackhead removing agent, the blackhead removing agent can be dried in a shorter period of time, after being applied onto the face or the like. Further, blackheads can be effectively removed.

The blackhead removing agent of the present invention contains a water-soluble macromolecular compound as a primary component.

A water-soluble macromolecular compound which exhibits adhesive when wet or moistened by a hydrophilic medium such as water or ethyl alcohol is preferably used as the water-soluble macromolecular compound that is to be contained in the blackhead removing agent of the present invention.

The water-soluble macromolecular compound that is to be contained in the blackhead removing agent of the present invention is not particularly limited, and a variety of water-soluble polymers can be used. Examples of such water-soluble macromolecular compounds include hydrophilic functional group-containing polyacrylic acid, polyacrylic acid alkyl ester copolymers, organosiloxane-based polymers, polyvinyl pyrrolidone, polyvinyl alcohols, cellulose derivatives, starches, alginates, poly(vinyl ether-maleic acid) copolymers, poly-N-vinyl acetamide, and copolymers of N-vinyl-2-pyrrolidone and vinyl acetate. Among these the water-soluble macromolecular compounds, a copolymer of N-vinyl-2-pyrrolidone and vinyl acetate is most preferable.

Water-soluble macromolecular compounds containing a copolymer of N-vinyl-2-pyrrolidone and vinyl acetate have suitable cohesion. Such water-soluble macromolecular compounds also have better spreadability on the surface of the skin as well as better adhesion (sticking properties) and the like. Such water-soluble macromolecular compounds are also better in that they do not irritate the skin.

The copolymerization ratio in copolymers of N-vinyl-2-pyrrolidone and vinyl acetate is preferably within the range of 5:95 to 95:5, more preferably 15:85 to 85:15, and even more preferably 30:70 to 70:30. A copolymerization ratio within this range allows a blackhead removing agent with good adhesion on the skin to be obtained. It also can improve the blackhead removing capabilities of the blackhead removing agent.

The copolymer of N-vinyl-2-pyrrolidone and vinyl acetate may be a copolymer of any form, such as a random copolymer, block copolymer, or graft copolymer.

The amount of the copolymer of N-vinyl-2-pyrrolidone and vinyl acetate in the blackhead removing agent is preferably about 15 to 95 wt %, and more preferably about 30 to 80 wt %. Too low a copolymer content, sometimes fails to improve the blackhead removing capabilities. On the other hand, too great a copolymer content, results in a blackhead removing agent with poor handling. Specifically, when the blackhead removing agent is dried, for example, the blackhead removing agent becomes too hard and thus cracks.

Therefore, if needed, a homopolymer component such as poly(N-vinyl-2-pyrrolidone), polyvinyl alcohol, or polyvinyl acetate may also be mixed with such a copolymer. By mixing such components, properties such as the cohesion and handling of the blackhead removing agent can be improved. Further, the strength of the blackhead removing layer after drying can be improved.

The weight-average molecular weight of the water-soluble macromolecular compound is preferably about 10,000 to 3,000,000, and more preferably about 20,000 to 1,500,000. A weight-average molecular weight of less than 10,000 sometimes lowers the mechanical strength of the blackhead removing agent when dried. A weight-average molecular weight of more than 3,000,000, on the other hand, can fail to provide good blackhead removing capabilities. Specifically, a weight-average molecular greater than 3,000,000 sometimes fails to provide a blackhead removing agent with good adhesion on the skin.

In the blackhead removing agent of the present invention, the amount of the plasticizer that is compatible with the aforementioned water-soluble macromolecular compound is less than 0.01 parts by weight with respect to 100 parts by weight of the water-soluble macromolecular compound. Thus, the time for drying the blackhead removing agent spread or applied on the skin can be shortened. Further, the mechanical strength of the blackhead removing agent in the dried condition can be improved since virtually no plasticizer that plasticizes the water-soluble macromolecular compound is contained. In consequence, it is possible to more efficiently remove blackheads from clogged pores.

To remove blackheads, the blackhead removing agent is initially spread on or applied in such a way that the blackhead removing agent adheres to the heads of the blackheads exposed from the pores. Then, the spread or applied blackhead removing agent is dried. The dried blackhead removing agent is finally peeled off. It should be noted that the blackhead removing efficiency varies depending on the direction in which the blackhead removing agent is peeled off when it is removed. This is described below with references to FIGS. 1 and 2.

FIG. 1 shows the state that blackheads are peeled off from skin by a blackhead removing sheet having sufficient mechanical strength. The solid-lined arrows in FIGS. 1 and 2 indicate the direction in which the blackhead removing sheet has been peeled off. The dotted-line arrows indicate the direction in which the blackheads are extracted.

In FIG. 1, a blackhead 2 is most efficiently removed without leaving the inner portion of the blackhead in the pore when extracted by force acting in the direction opposite the depthwise direction of the pore (that is, the direction virtually perpendicular to the surface of the skin 3). Thus, as shown in FIG. 1, the angle θ at the peeling portion 4 between the surface of the skin 3 and the blackhead removing layer of the blackhead removing sheet 1 is preferably about 90°, and more preferably less than 90°. Peeling off of the blackhead removing sheet 1 in this manner allows the blackhead 2 to be extracted substantially perpendicularly to the surface of the skin 3. The blackhead 2 can furthermore be completely removed from the pore by being extracted in the direction virtually perpendicular to the surface of the skin 3. In order to achieve such effects, it is necessary for the blackhead removing sheet 1 to have a certain level of hardness (mechanical strength) in the dried condition.

The blackhead removing agent of the present invention contains virtually no plasticizer that is compatible with the water-soluble macromolecular compound in the blackhead removing agent. Specifically, the amount of the plasticizer in the blackhead removing agent of the present invention is less than 0.01 parts by weight with respect to 100 parts by weight of the water-soluble macromolecular compound. Therefore, according to the blackhead removing agent of the present invention, the "dryness" and the "mechanical strength in the dried condition" can be improved. The blackhead removing agent of the present invention also allows blackheads to be extracted substantially perpendicularly to the surface of the skin, and thus allows blackheads to be efficiently removed.

Figure 2:
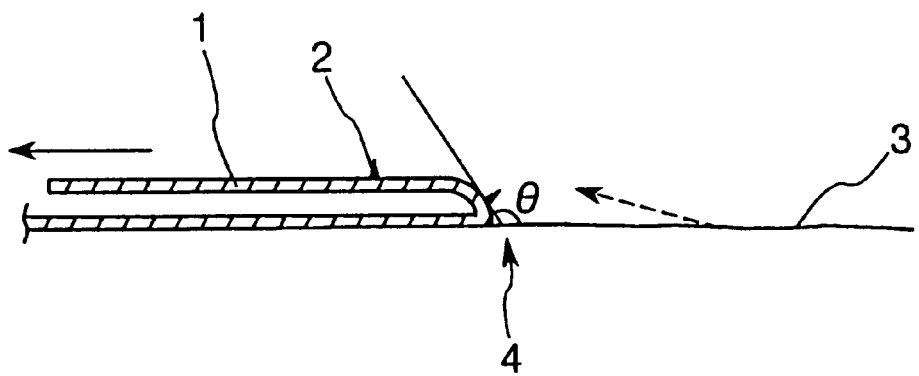
FIG. 2 shows the state that blackheads are peeled off from the skin using a conventional blackhead removing sheet.

However, if blackhead removing sheets do not have sufficient mechanical strength in the dried condition, blackheads cannot be completely removed from pores. A specific example of such a blackhead removing sheet having insufficient mechanical strength is shown in FIG. 2. FIG. 2 shows the state that blackheads are peeled off from the skin by a conventional blackhead removing sheet having insufficient mechanical strength.

The blackhead removing sheet 1 is peeled off while folded, as shown in FIG. 2, when the blackhead removing sheet has insufficient mechanical strength in the dried condition. In FIG. 2, the angle θ at the peeling portion 4 between the surface of the skin 3 and the blackhead removing layer of the blackhead removing sheet 1 is far greater than 90°. Thus, it is difficult to extract the blackhead 2 substantially perpendicular to the surface of the skin 3 as shown in FIG. 1.

When blackheads are removed in the manner shown in FIG. 2, there is a case that the blackhead 2 cannot be completely removed from the depths of the pore. The reason is that, when the blackhead 2 is brittle, the blackhead 2 breaks while being extracted, leaving part of the broken blackhead in the depths of the pore.

In this connection, it should be noted that the relation between the mechanical strength of the blackhead removing sheet and the angle at which the blackhead is extracted as described with reference to FIGS. 1 and 2 applies not only to the blackhead removing sheet but also to the peel-off type of blackhead removing agent.

As described above, the amount of the plasticizer in the blackhead removing agent of the present invention is less than 0.01 parts by weight with respect to 100 parts by weight of the water-soluble macromolecular compound. Polyhydric alcohols are included in examples of such plasticizers. Examples of such polyhydric alcohols include ethylene glycol, diethylene glycol, triethylene glycol, and higher polyethylene glycols; propylene glycol and higher polypropylene glycols; 1,3-butanediol, 1,4-butanediol, and other butanediols; glycerin, diglycerin, triglycerin, and other polyglycerins; and the like.

Plasticizers with a boiling point of 120° C. or higher at ordinary pressure among the above are difficult to be volatilized at temperatures from room temperature to around body temperature. Thus, the blackhead removing agent tends to take a longer time to dry after being spread or applied on the skin. Glycols and the like also have water retention effects, and thus tend to prevent the blackhead removing agent from drying sufficiently in a short period of time. Thus, the blackhead removing agent of the present invention preferably contains virtually no plasticizer of this type.

The blackhead removing agent of the present invention contains a filler. This allows the blackhead removing agent to be dried in a shorter period of time. It also allows the mechanical strength of the dry film to be increased. Thus, the blackhead removing agent can be completely removed without leaving any partial residue, when the blackhead removing agent spread (applied) on the skin is peeled off and removed.

The filler is preferably in the form of a powder. The powder configuration is not particularly limited. For example, the powder in the filler may be in the form of spheres, scales, needles, or the like. Among these shapes, the spherical powder is particularly preferable in view of dispersion.

The mean particle diameter of the filler is preferably 5 nm to 50 μm, and more preferably 7 nm to 30 μm. By setting the particle diameter of the powder in the filler within such a range, it is possible to disperse effectively the filler into the blackhead removing agent or blackhead removing layer.

The amount of filler is preferably less than 120 parts by weight and more preferably within 1 to 100 parts by weight, with respect to 100 parts by weight of water-soluble macromolecular compound.

If the amount of filler is 0 parts by weight, the mechanical strength of the dry film of the dried blackhead removing agent cannot be improved. Therefore, there is a case that portions of the blackhead removing agent are left on the skin. Further, there is a case that the drying time for the blackhead removing agent cannot be shortened. On the other hand, if the amount of filler is more than 120 parts by weight, there is a possibility to cause discomfort when the blackhead removing agent is spread or applied to the skin. Further, there is a case that the blackhead removing capabilities are reduced.

The filler to be used in the present invention is not particularly limited. Examples of fillers which can be used include inorganic fillers, organic fillers, and mixtures thereof. The blackhead removing agent of the present invention preferably contains an inorganic filler as a primary component. When an inorganic filler is contained as a primary component, the moisture absorption properties of the inorganic filler allow moisture in the blackhead removing agent or blackhead removing layer to be absorbed. Thus, the time needed to dry the blackhead removing agent can be shortened, and the mechanical strength of the dried blackhead removing agent can be improved.

Examples of inorganic fillers include zinc oxide, titanium dioxide, silica, alumina, barium sulfate, zirconium oxide, calcium carbonate, calcium silicate, ceramics, hydroxyapatite, boron nitride, sericite, mica, talc, clay, kaolin, montmorillonite, hectorite, saponite, black iron oxide, yellow iron oxide, red iron oxide, Prussian blue, ultramarine, carbon black, and pearlescent pigments. In this connection, these may be used alone or in combinations of two or more. The blackhead removing agent of the present invention preferably contains silica and titanium dioxide among these.

Silica has water-absorption action, and can absorb the moisture contained in the blackhead removing agent or the blackhead removing layer. Thus, silica can be used to improve the drying properties. Further, it is possible to improve the strength of the dry film of the blackhead removing agent or blackhead removing layer. Furthermore, it is possible to provide the blackhead removing agent with better peeling properties.

Since, titanium dioxide has white masking properties, it is possible to whiten the blackhead removing agent by adding the titanium dioxide. Thus, it becomes possible to easily find blackheads which have been removed from pores and which adhere to the blackhead removing agent or blackhead removing layer.

Examples of organic fillers include those consisting of silk powder, cellulose powder, polyacrylic acid ester resins, polymethacrylic acid ester resins, polyamide resins, polyolefin resins, polyimide resins, polyurethane resins, polyester resins, polyether resins, polyvinyl chloride resins, urea resins, polyformamide resins, polycarbonate resins, polyvinyl acetate resins, polyvinylidene chloride resins, polyacrylonitrile resins, polysulfone resins, polystyrene resins, polyurea resins, silicone resins, melamine resins, polytetrafluorethylene resins, Lake pigments, and azo pigments. These may be used alone or in combinations of two or more if needed.

Particles for the aforementioned inorganic filler or organic filler may be of a porous form. Such porous particles may contain drugs such as bactericides, for example.

The particles of the aforementioned inorganic filler or organic filler may be coated with various types of functional polymers or the like.

The blackhead removing agent of the present invention preferably contains a solvent. Such solvents are not particularly limited. However, it is preferable to use the solvent that should dissolve the aforementioned water-soluble macromolecular compound in a stable manner, should be volatile at room temperature to around body temperature, and should not irritate the skin. For example, water and/or a $C_1$ to $C_4$ monohydric alcohol, such as water, ethanol, or isopropyl alcohol are preferably used as the solvent.

The amount of the solvent in the blackhead removing agent can be suitably determined depending on the type of water-soluble macromolecular compound, the amount of the filler, the type of blackhead removing agent, and the like. The amount of the solvent in the blackhead removing agent is preferably about 20 to 500 parts by weight with respect to 100 parts by weight of the water-soluble macromolecular compound.

If the blackhead removing agent is used by individuals that are sensitive to dermal irritation, there is a danger of irritation to the skin when the blackhead removing agent is peeled off of the skin. To control such irritation by the blackhead removing agent, the blackhead removing agent of the present invention may contain a hydrocarbon such as squalane, squalene, Vaseline, or liquid paraffin; a natural oil such as jojoba oil, castor oil, olive oil, egg yolk oil, or coconut oil; a silicone oil such as polydimethylsiloxane; a higher fatty acid such as oleic acid or isostearic acid; a higher alcohol such as lauryl alcohol; an ester such as isopropyl myristate; or another such oily component.

In order to ensure that such oil components are uniformly dispersed in the blackhead removing agent, the agent may also contain nonionic surfactants such as glycerin fatty acid ester, sorbitan fatty acid ester, polyoxyethylene sorbitan fatty acid ester, polyoxyethylene castor oil, polyoxyethylene hydrogenated castor oil, and polyoxyethylene alkyl ether; anionic surfactants such as N-acylamino acid salts; cationic surfactants such as aliphatic quaternary ammonium salts; amphoteric surfactants such as betaines; and silica which have undergone hydrophobic surface treatment, such as polymethylsiloxane.

In the blackhead removing agent of the present invention, various additives used in cosmetics, medicinal preparations, and the like may also be blended. Examples of such additives include bactericides, viscosity regulators, preservatives, mildewcides, fragrances, humectants, physiologically active components, salts, antioxidants, neutralizers, pH regulators, anti-inflammatories, and nutrients.

The blackhead removing agent of the present invention may also contain additives such as vinyl alcohol, vinyl alkyl ethers, styrene, alkyl-substituted styrenes, acrylic acid, methacrylic acid, acrylic acid esters, methacrylic acid esters, vinyl butyral, vinyl formal, acrylamide, N-alkyl acrylamides, N-vinyl acetamide, allylamine, ethyleneimine, acrylonitrile, α-amino acids, styrenesulfonic acid, salts of α-amino acids and styrenesulfonic acid, and other common monomer homopolymers or copolymers.

The blackhead removing agent of the present invention may also contain additives such as alginic acid, alginates, starches, cellulose, cellulose derivatives (HEC and CMC), and other such macromolecular compounds. The amount of such macromolecular compounds is not particularly limited, but is preferably 20 wt % or less, and more preferably about 0.1 to 10 wt %, relative to the blackhead removing agent.

The blackhead removing agent of the present invention can be used as a peel-off type of blackhead removing agent. A peel-off type of blackhead removing agent refers to a liquid blackhead removing agent. Such peel-off types of blackhead removing agents can be applied directly by hand, for example, around the nose, on the forehead, on the chin, on the cheeks.

The blackhead removing agent of the present invention may be formed in layers and used as a material for blackhead removing sheets. A blackhead removing sheet refers to a sheet-type blackhead removing agent, comprising a layered blackhead removing agent laminated onto a base layer consisting of a fabric such as woven or nonwoven fabric, a base layer consisting of paper, or a base layer consisting of a film, or the like.

According to the sheet-type blackhead removing agent (blackhead removing sheet) described above, it is not necessary to directly contact the blackhead removing agent when used. Thus, it is possible to prevent the blackhead removing agent from soiling the fingers when the blackhead removing sheet is applied to the skin.

Further, according to the blackhead removing sheet of the present invention, the layered blackhead removing agent is laminated on the base layer. Thus, the blackhead removing agent can be applied easily and uniformly on the skin.

The blackhead removing sheet of the present invention is described below with reference to FIGS. 3 and 4.

Figure 3:
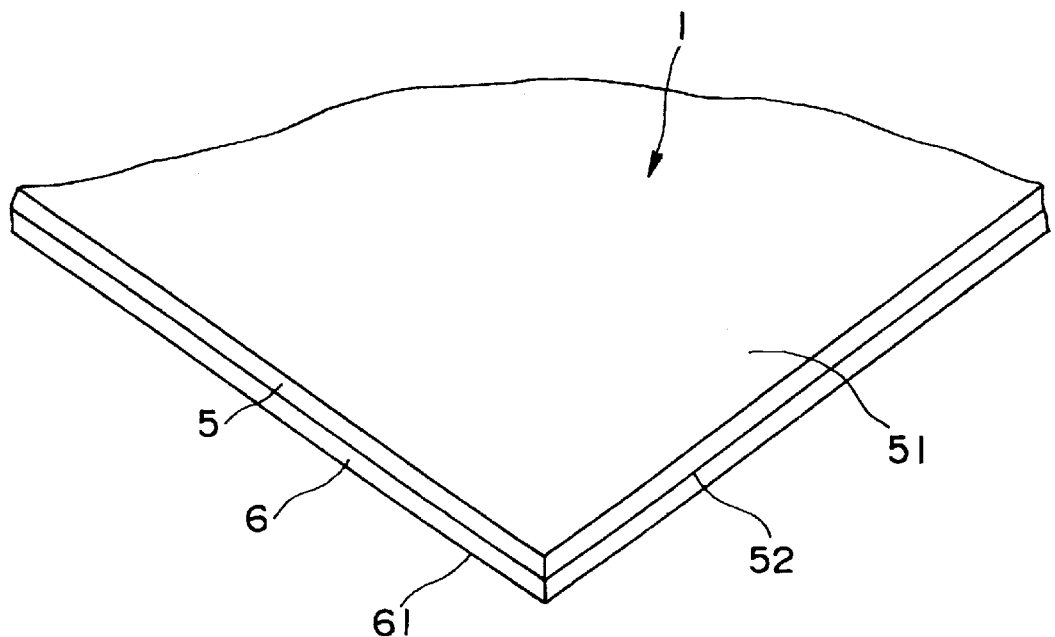
FIG. 3 is a perspective view of an embodiment of the blackhead removing sheet of the present invention.

FIG. 3 is a perspective view showing an example of the structure of the blackhead removing sheet of the present invention. FIG. 4 is a cross sectional view showing the blackhead removing sheet of the present invention.

The blackhead removing sheet 1 of the present invention is composed of a base layer 5 and a blackhead removing layer 6 consisting of a blackhead removing agent. The blackhead removing layer 6 in the blackhead removing sheet 1 is laminated onto the base layer 5, as shown in FIG. 3.

Figure 4:
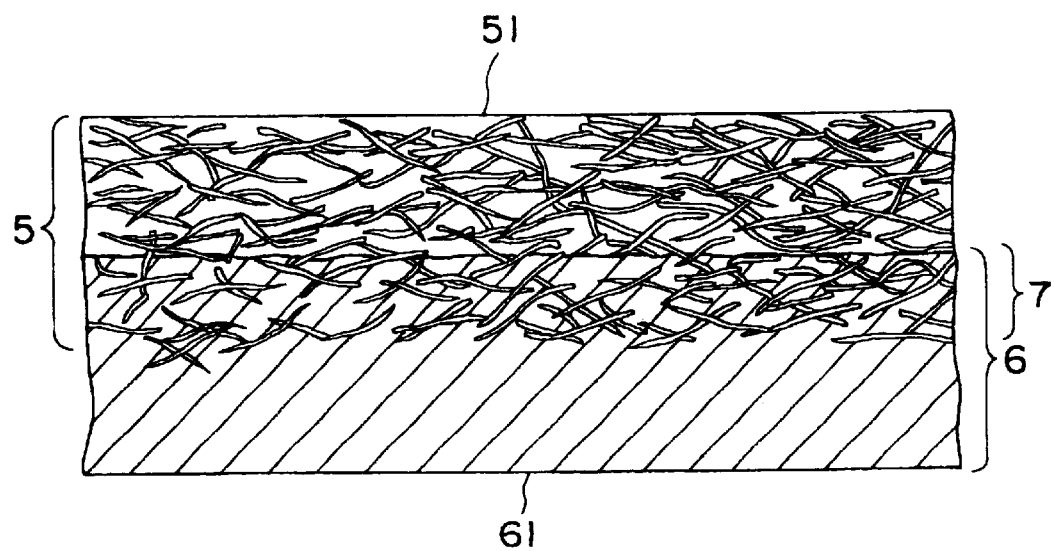
FIG. 4 is a cross sectional view showing the blackhead removing sheet of the present invention.

The base layer 5 and blackhead removing layer 6 are overlapped near the interface between the base layer 5 and blackhead removing layer 6, as shown in FIG. 4. This overlapped portion is indicated as an overlapped part 7 in FIG. 4.

The structure of a laminate having such an overlapped part 7 requires no adhesive or the like between the base layer 5 and blackhead removing layer 6. Further, the base layer 5 and blackhead removing layer 6 can be easily and firmly unified. By firmly unifying the base layer 5 and blackhead removing layer 6, it becomes possible to prevent the base layer 5 from separating from the blackhead removing agent 6 when the blackhead removing sheet 1 is peeled off. Thus, it becomes possible to prevent some of the blackhead removing agent from remaining on the skin when the blackhead removing sheet 1 is peeled off.

At the overlapped part 7, part of the blackhead removing layer 6 impregnates into or becomes embedded in the base layer 5. In the present invention, the overlapped part 7 should preferably have a thickness about 1 to 65%, and more preferably about 5 to 50%, of the thickness of the base layer 5 as a whole.

If the ratio mentioned above is too small, the blackhead removing layer 6 has weaker adhesive strength on the base layer 5. As a result, when the blackhead removing sheet 1 is peeled off from the skin, the base layer 5 runs the risk of separating from the blackhead removing layer 6. On the other hand, if the ratio is too great, there is a possibility of the blackhead removing agent exuding from the outer surface (surface 51) of the base layer 5 opposite the surface to which the blackhead removing layer 6 is laminated, when the blackhead removing layer 6 is moistened or wet with a hydrophilic medium such as water. When the blackhead removing agent is exuded from the surface 51, it arises a problem in that handleability and blackhead removing capability of the blackhead removing sheet 1 are lowered.

The laminated base layer 5 of the blackhead removing sheet 1 of the present invention serves to support the blackhead removing layer 6. The base layer 5 allows the blackhead removing sheet 1 to be readily applied to the skin. The base layer 5 also allows the blackhead removing sheet 1 to be readily peeled off from the skin.

Examples of materials for the base layer 5 to be used in the blackhead removing sheet of the present invention include materials that have sufficient mechanical strength, that do not interfere with the dry of the blackhead removing layer 6 after application, and that do not interfere with the conformability to be curved surface. In this connection, gas-permeable and flexible (soft) materials are preferably used as the material for the base layer 5.

When a gas-permeable material is used as the base layer 5, the time needed to dry the blackhead removing layer 6 can be shortened. When a flexible material is used as the base layer 5, the blackhead removing sheet 1 can have better conformability on the skin. In other words, the blackhead removing sheet 1 can be provided with the better adhesion needed to remove blackheads.

The structural material of such a base layer 5 may be a porous material, for example. Examples of such porous materials include those composed of nonfibrous or fibrous materials.

When the base layer 5 is made of a porous material, the flexibility can be improved. Specifically, the blackhead removing sheet can be easily and closely applied to protuberant areas such as the nose.

Furthermore, when the base layer 5 is made of a porous material, the time needed to dry the blackhead removing layer 6 can be considerably shortened.

Examples of nonfibrous porous materials include materials in the form of sheets, such as membrane filters, foams (such as foamed polypropylene, foamed polyethylene, and foamed polyurethane), various types of porous films, and meshes.

Examples of fibrous porous materials include weaves, nonwoven fabrics, paper, and short fiber agglomerates. Here, weaves include knits and weaves such as woven fabrics, and other similar materials.

Any type of material suitable for practical use can be used as the weave. For example, plain weaves, twill weaves, and crepe weaves can be used as the weave.

Knits are not particularly limited. Examples of such knits include weft knits (plain knits), warp knits (tricot knits), purl knits, flattened knits, and stockinet knits.

Examples of paper include ordinary paper (Western or Japanese style paper), laminates of ordinary paper, and various types of synthetic paper.

Examples of fiber constituents of such fibrous porous materials include natural fibers such as cellulose fibers, cotton, linter, kapok, flax, hemp, ramie, silk, and wool; and chemical fibers such as nylon (polyamide), tetron, rayon, cupra, acetate, vinylon, acrylic, polyethylene terephthalate (polyester), and polypropylene. These fibers can be used alone or in suitable combinations of two or more. In this connection, the thickness of the fibers is selected according to type and properties.

The base layer 5 can be composed of nonwoven fabric consisting of the ultrafine denier fibers described below. By using such materials, it becomes possible to provide a blackhead removing sheet which has the desired gas permeability and flexibility (softness) as well as better conformability to the curved surfaces of the skin and better feel on the skin.

Nonwoven fabric consisting of ultrafine denier fibers can be used to prevent the blackhead removing agent from penetrating too far into the nonwoven fabric. Thus, it becomes possible to provide a blackhead removing sheet with a blackhead removing layer capable of exhibiting satisfactory blackhead removing properties, using a relatively low amount of blackhead removing material. The blackhead removing layer can be composed of a low amount of blackhead removing material to shorten the time needed to dry the blackhead removing layer required during the manufacture of the blackhead removing sheet and the use of the blackhead removing sheet.

Examples of constituent fibers for such nonwoven fabrics include the same fibers used to form the aforementioned fibrous porous materials.

The denier of the constituent fibers of the nonwoven fabric is 0.0001 denier or more but less than 0.1 denier, preferably about 0.0003 to 0.07 denier, and even more preferably about 0.0005 to 0.04 denier.

When fibers have a denier of 0.1 or more, greater amounts of blackhead removing agent are absorbed by the fibers, depending on the type of fiber or the like. Such cases are economically disadvantageous because greater amounts of blackhead removing agent are required to provide a blackhead removing layer. When the fibers absorb greater amounts of blackhead removing agent, the blackhead removing sheet cannot be dried in a short period of time. However, on the other hand, it is difficult to manufacture fibers with a denier of less than 0.0001.

By forming the base layer 5 with a nonwoven fabric consisting of ultrafine denier fibers having the aforementioned denier, it becomes possible to increase the filling density (bulk density) of fibers without increasing their thickness. Accordingly, the blackhead removing agent that is applied to the base layer 5 during manufacture, and the blackhead removing agent that is moistened and softened during use or the like, can be prevented from penetrating too deeply into the gaps between the fibers. As a result, the thickness of a portion of the removing layer 6 which is not overlapped on the base layer 5 can be sufficiently ensured, thereby enabling to obtain better blackhead removing capabilities.

Further, by forming the base layer 5 with a nonwoven fabric consisting of ultrafine denier fibers having the aforementioned denier, it becomes possible to prevent the blackhead removing agent from exuding from the surface 51 of the base layer 5. This prevents the hands of the user from becoming soiled by the blackhead removing agent when gripping the base layer 5 of the blackhead removing sheet, for example.

Furthermore, by forming the base layer 5 with a nonwoven fabric consisting of ultrafine denier fibers having the aforementioned denier, it becomes possible to provide the blackhead removing sheet with better softness. In other words, the blackhead removing sheet 1 can have better conformability to the curved surfaces.

The thickness of the base layer 5 is suitably determined according to the structural material, denier, filling density, and the like. In this case, the base layer 5 has preferably a thickness of about 0.05 to 1 mm, more preferably about 0.07 to 0.7 mm, and even more preferably about 0.1 to 0.5 mm.

When the thickness of the base layer 5 is less than 0.05 mm, the blackhead removing agent tends to exude from the surface 51 of the base layer 5. On the other hand, when the base layer 5 is more than 1 mm thick, the base layer 5 is less soft, thus leading to a decreased conformability of the base layer 5 to the skin.

The basis weight of the base layer 5 is preferably about 20 to 200 g/m$^2$, and more preferably about 30 to 100 g/m$^2$. When the basis weight is too low, there is a case that it will no longer be possible to effectively prevent the blackhead removing agent from penetrating deeply into the gaps between the fibers. On the other hand, if the basis weight is too great, softness of the base layer 5 is lowered, thus making it impossible to ensure adequate conformability to the curved surface.

The surface of the base layer 5 may undergo hydrophilic pre-treatment or hydrophobic (water repellent) pre-treatment. The structural material of the base layer 5 may also undergo such hydrophilic pre-treatment or hydrophobic (water repellent) pre-treatment.

Thus, by applying the above-mentioned treatment onto the surface of the base layer 5 or the structural material of the base layer 5, it becomes possible to control the drying rate of the blackhead removing layer 6. It is also possible to adjust the thickness of the overlapped part 7 (see FIG. 4) constituted by the base layer 5 and blackhead removing layer 6.

The aforementioned hydrophilic treatment may be carried out at the surface 52 of the base layer 5 which is joined with the blackhead removing layer 6, for example. Further, the aforementioned hydrophobic (water repellent) treatment may be carried out on the outer surface (surface 51) of the base layer 5 opposite the surface to which the blackhead removing layer 6 is laminated, for example. Furthermore, both hydrophilic and hydrophobic treatments may also be carried out on both sides of the base layer 5.

When a hydrophilic treatment is carried out on the laminating surface 52, the adhesive strength of the blackhead removing layer 6 on the base layer 5 can be improved.

When a hydrophobic treatment is carried out on the surface 51, the overlapped part 7 can be made thinner. This makes it possible to prevent the blackhead removing agent from being exuded from the surface of the base layer 5. This also makes it possible to improve the blackhead removing capabilities.

Examples of hydrophilic treatment include application of surfactants and plasma treatment. Examples of hydrophobic (water repellent) treatment include application of silicone compound water repellents or fluorine compound water repellents.

The base layer 5 of the blackhead removing sheet of the present invention may also be composed of a laminate. Such a laminate may be constructed by laminating a plurality of different layers. A laminates composed of any selected combination from among hydrophilic treated nonwoven fabric, hydrophobic (water repellent) treated nonwoven fabric, and nonwoven fabric which has neither been hydrophilic nor hydrophobic (water repellent) treated can be used as the base layer 5. The same effects as those described above can be obtained in this case as well.

The blackhead removing layer 6 is composed of the aforementioned blackhead removing agent.

As described above, according to the blackhead removing sheet of the present invention, the blackhead removing sheet has the laminate comprising the base layer 5 and the blackhead removing layer 6. The base layer 5 consists of a nonwoven fabric composed of the aforementioned ultrafine denier fibers. The blackhead removing layer 6 is laminated onto the base layer 5. Further, the blackhead removing layer 6 of the blackhead removing sheet is composed of a blackhead removing agent including water-soluble macromolecular compound, filler, and plasticizer that is compatible with the aforementioned water-soluble macromolecular compound. The amount of plasticizer contained in the blackhead removing layer 6 is less than 0.01 parts by weight with respect to 100 parts by weight of water-soluble macromolecular compound. This allows the time needed to dry the blackhead removing sheet to be shortened. The blackhead removing capabilities and the like of the blackhead removing sheet can also be improved.

The thickness of the blackhead removing layer 6 is not particularly limited. The thickness of the blackhead removing layer 6 is preferably 0.05 to 1 mm, and more preferably 0.08 to 0.3 mm.

When the blackhead removing layer 6 is too thin, the blackhead removing layer 6 has lower strength. As a result, when the blackhead removing sheet is peeled off from the skin, there is a case that the blackhead removing layer 6 is broken, and then some of the blackhead removing agent are left on the skin.

Furthermore, when the blackhead removing layer 6 is too thin, it is difficult to keep the thickness of the overlapped part 7 at or beyond the predetermined size. As a result, the bonding strength of the blackhead removing layer 6 on the base layer 5 is inadequate, leading to the danger of interlaminar peeling.

On the other hand, when the blackhead removing layer 6 is too thick, it sometimes takes a long time for the blackhead removing layer 6 to dry after the blackhead removing sheet 1 has been applied.

The method for forming the blackhead removing layer 6 in the blackhead removing sheet of the present invention is not particularly limited. The blackhead removing layer 6 is preferably formed by a coating or transfer method because of the ease of forming, stability, productivity, and the like. The blackhead removing layer 6 can be easily and uniformly formed using a coating or transfer method. The blackhead removing sheet can be formed in such a way that part of the blackhead removing layer 6 is allowed to impregnate into the interior of the base layer 5. The blackhead removing sheet can also be formed by adjusting the thickness of the overlapped part 7.

The blackhead removing sheet of the present invention may be composed of a laminate containing only a base layer 5 and a blackhead removing layer 6. Further, in the blackhead removing sheet of the present invention, an interlayer such as an adhesive layer may also be interposed between the base layer 5 and the blackhead removing layer 6 in order to join the base layer 5 and blackhead removing layer 6.

In the blackhead removing sheet 1 of the present invention, the loss on drying is preferably 3 to 30%. Here, the loss on drying corresponds to the amount of solvent contained in the blackhead removing sheet, and can be determined by the following Equation (1).

$$\text{Loss on drying } [\%] = \{(W_A - W_B)/W_A\} \times 100 \quad (1)$$

$W_A$: weight of blackhead removing sheet before drying
$W_B$: weight of blackhead removing sheet after drying When the loss on drying is less than 3%, there is a case that the blackhead removing layer 6 will be cracked. Further there is a case that the blackhead removing layer 6 will be peeled off from the base layer 5.

When the loss on drying is greater than 30%, there is a risk that the blackhead removing agent can be exuded from the base layer surface and the ends of the sheet. Another concern is that the fingers will become soiled by blackhead removing agent exuding from the surface of the base layer when the blackhead removing sheet is applied. Another concern is that blackhead removing agent exuding from the ends of the sheet will remain on the skin when the blackhead removing sheet is peeled off.

In the blackhead removing sheet of the present invention, the outer surface (surface 51) of the base layer 5 opposite the surface to which the aforementioned blackhead removing layer 6 is laminated may be provided with a protective layer in order to control volatilization of the blackhead removing layer component of the blackhead removing sheet, as well as in order to prevent the surface of the base layer from becoming stained, or the like.

Examples of such protective layers include films consisting of polyester, polyethylene, polypropylene, or the like; polymer surface-treated paper; and other films and sheets.

In the blackhead removing sheet of the present invention, a release liner film is preferably provided on the outer surface (application surface 61) of the blackhead removing layer 6 opposite the surface to which the base layer 5 is laminated. By providing such a release liner film, it becomes possible to ensure the sanitary storage of the blackhead removing layer 6 until use, and to control the volatilization of components in the blackhead removing layer.

Examples of such a release liner film include any commonly used release liner film. Specific examples include films consisting of polyester, polyethylene, polypropylene or the like, which have been coated with an exfoliation agent such as silicone on the side joined with the application surface 61; polymer surface-treated paper; and other films and sheets.

The blackhead removing sheet of the present invention can be produced in the following manner, for example.

1. Coating Method

The blackhead removing agent is prepared. The blackhead removing agent may be prepared in the following manner, for example. First, a predetermined amount of a filler and a predetermined amount of a water-soluble macromolecular compound such as a copolymer of vinyl acetate and N-vinyl-2-pyrrolidone are mixed with each other. Further, if required, additives such as preservatives and solvents or the like can also be mixed in the predetermined amounts. Finally, these are stirred to prepare the blackhead removing agent. In this connection, the viscosity of the blackhead removing agent should generally be about 100 to 5,000 cps at ordinary temperature.

Next, a base layer 5 composed of a nonwoven fabric of ultrafine denier fibers is prepared. Then, the blackhead removing agent which has been prepared is applied to one side of the base layer 5 and is dried.

The impregnation of the base layer 5 by the blackhead removing agent can be suitably controlled here because the base layer 5 is composed of a nonwoven fabric of ultrafine denier fibers. The proportion of the impregnated part relative to the thickness of the base layer 5 can also be kept within the aforementioned range. The blackhead removing agent can also be prevented from being exuded from the surface 51 of the base layer 5. It is also possible to produce a blackhead removing sheet with excellent blackhead removing capabilities by using a low amount of the blackhead removing agent.

Examples of methods for applying the blackhead removing agent to the base layer 5 include dipping, brushing, spray coating, and coating using roller, air knife, knife, conma, gravure, mayer bar, fountain die, or the like. Any of these methods may be used.

Such coating methods allow the blackhead removing agent to impregnate into the gaps between the fibers of the nonwoven fabric constituting the base layer 5. In this case, as shown in FIG. 4, the blackhead removing agent can be applied in such a way as to allow a part of the blackhead removing layer 6 to impregnate into or become embedded in the base layer 5.

As described above, a hydrophilic pre-treatment or hydrophobic (water repellent) pre-treatment may be carried out on the surface of the base layer 5. The structural material of the base layer 5 may also be subjected to a hydrophilic pre-treatment or hydrophobic (water repellent) pre-treatment.

2. Transfer Method

A blackhead removing agent is prepared in the same manner as above. Then, the blackhead removing agent is applied to the surface of a transfer medium (intermediate) such as a film or sheet, and is dried to form a blackhead removing layer 6. The release liner films described above can be used as a transfer medium.

Next, the blackhead removing layer 6 is overlapped onto the base layer 5, and the blackhead removing layer 6 is transferred to the surface of the base layer 5. After the transfer has been completed, the transfer medium may be removed as needed. According to such a transfer method, as shown in FIG. 4, the blackhead removing agent can be applied in such a way that a part of the blackhead removing layer 6 impregnates into or is embedded in the base layer 5.

When the blackhead removing layer 6 is transferred to the base layer 5, the blackhead removing layer 6 may be hydrated as needed in order to improve the adhesive strength of the blackhead removing layer 6 to the base layer 5. Further, moistening and pressurizing treatments may be carried out after the blackhead removing layer 6 has been overlapped on the base layer 5.

When the blackhead removing layer 6 is transferred onto a base layer 5, an interlayer such as an adhesive layer may be provided between the base layer 5 and blackhead removing layer 6.

The base layer 5 may also be subjected to a hydrophilic pre-treatment or hydrophobic (water repellent) pre-treatment in the same manner as in the coating method.

According to the aforementioned method for producing the blackhead removing sheet of the present invention, a blackhead removing sheet which can exhibit excellent effects can be easily manufactured. In addition, the thickness of the base layer 5, the thickness of the blackhead removing layer 6, the thickness of the part where the base layer 5 and blackhead removing layer 6 overlap, and the like can also be easily controlled. A blackhead removing layer 6 can also be formed to a virtually even thickness.

The blackhead removing agent used in the method for producing the blackhead removing sheet of the present invention comprises a water-soluble macromolecular compound, a filler, and a plasticizer that is compatible with the water-soluble macromolecular compound. The amount of the plasticizer in the blackhead removing agent is less than 0.01 parts by weight with respect to 100 parts by weight of water-soluble macromolecular compound. Using such a blackhead removing agent, it is possible to shorten the time needed to dry the blackhead removing layer 6 in the manufacturing process. Therefore, a blackhead removing sheet can be produced more efficiently.

EXAMPLES

Specific examples of the present invention are described below.

1. Production of Blackhead Removing Sheet

Example 1

A blackhead removing agent having the following composition was prepared.

First, the fillers and the like were added to a solution of a water-soluble macromolecular, and the ingredients were thoroughly stirred, thereby preparing a blackhead removing agent. The prepared blackhead removing agent had a viscosity of 500 to 1500 cps at ordinary temperature.

Water-soluble macromolecular compound: 100 parts by weight of copolymer of N-vinyl-2-pyrrolidone and vinyl acetate Filler: 20 parts by weight of silica and 1 parts by weight of titanium dioxide, with respect to 100 parts by weight of N-vinyl-2-pyrrolidone and vinyl acetate Solvent: 50 parts by weight of water and 50 parts by weight of ethanol, with respect to 100 parts by weight of N-vinyl-2-pyrrolidone and vinyl acetate Additives: 0.1 parts by weight of preservative with respect to 100 parts by weight of N-vinyl-2-pyrrolidone and vinyl acetate The aforementioned blackhead removing agent was applied onto the treated surface of a polyethylene terephthalate film which had been release treated on one side with a silicone-based exfoliation agent, and then it was dried, to form a blackhead removing layer that was 0.17 mm thick (thickness of the layer when dried).

A polyester nonwoven fabric (fineness: 0.0007 denier; basis weight: 40 g/m$^2$; thickness: 0.45 mm) serving as the base layer was overlapped on the blackhead removing layer, forming a three-layered blackhead removing sheet consisting of the release liner film, the blackhead removing layer and the base layer.

Table 1 shows the blackhead removing layer composition, the thickness of the part where the base layer and blackhead removing layer are overlapped, and the like.

Example 2

A blackhead removing sheet was prepared in the same manner as in Example 1 except that the composition of the water-soluble macromolecular compound was altered.

Example 3

A blackhead removing sheet was prepared in the same manner as in Example 1 except that the composition of the water-soluble macromolecular compound was altered.

Example 4

A blackhead removing sheet was prepared in the same manner as in Example 1 except that the composition of the water-soluble macromolecular compound was altered.

Example 5

A blackhead removing sheet was prepared in the same manner as in Example 1 except that the amounts in which the fillers were blended were altered (the amount of the silica was increased).

Example 6

A blackhead removing agent having the composition shown in Table 2 was prepared. First, the fillers and the like were added to a solution of a water-soluble macromolecular compound, and the ingredients were thoroughly stirred to obtain a blackhead removing agent. The obtained blackhead removing agent had a viscosity of 500 to 1500 cps at ordinary temperature.

A nonwoven fabric consisting of acrylic ultrafine denier fibers (fineness: 0.0007 denier; basis weight: 40 g/m$^2$; thickness: 0.3 mm) was meanwhile prepared as the base layer.

The blackhead removing agent was applied on one side (laminating surface 52) of the base layer and was dried to form a blackhead removing layer having the thickness of 0.15 mm (thickness of the layer when dried), resulting in a blackhead removing sheet. The thickness of the part where the base layer and blackhead removing layer are overlapped was about 20% of the thickness of the base layer.

Example 7

A blackhead removing agent with the composition shown in Table 2 was prepared in the same manner as in Example 6.

A nonwoven fabric consisting of polyester ultrafine denier fibers (fineness: 0.005 denier; basis weight: 40 g/m$^2$; thickness: 0.35 mm) was meanwhile prepared as the base layer.

An exfoliation agent-coated polyethylene terephthalate film was then used as a transfer medium, and the blackhead removing agent was applied on the exfoliation agent layer of the film and was dried to form a blackhead removing layer having the thickness of 0.14 mm (thickness of the layer when dried).

The blackhead removing layer and the aforementioned base layer were overlapped, and the blackhead removing layer and base layer were joined by roll pressurization while moistened by hydration. The thickness of the part where the base layer and blackhead removing layer are overlapped was about 30% of the thickness of the base layer.

Example 8

A blackhead removing sheet was prepared in the same manner as in Example 6 except that a fiber blend of polyester ultrafine denier fibers and polypropylene ultrafine denier fibers (fineness (mean): 0.02 denier; basis weight: 50 g/m$^2$; thickness: 0.45 mm) was used as the base layer.

The thickness of the blackhead removing layer was 0.14 mm (thickness of the layer when dried), and the thickness of the part where the base layer and blackhead removing layer are overlapped was about 20% of the thickness of the base layer.

Example 9

A blackhead removing sheet was prepared in the same manner as in Example 6 except that the same nonwoven fabric that was used as the base layer in Example 6 was subjected to a hydrophobic pre-treatment on one side (surface 51) of the base layer, while the other side (laminating surface 52) was subjected to a hydrophilic pre-treatment.

The hydrophobic treatment was carried out by coating the surface 51 with a binder-diluted silicone-based water repellent, while the hydrophilic treatment was carried out by spray drying a surfactant on the laminating surface 52.

The thickness of the blackhead removing layer was 0.15 mm (thickness of the layer when dried), and the thickness of the part where the base layer and blackhead removing layer overlapped was about 25% of the thickness of the base layer.

Example 10

A blackhead removing sheet was prepared in the same manner as in Example 7 except that one side (surface 51) of the base layer was subjected to a hydrophobic pre-treatment, while the other side (laminating surface 52) was subjected to a hydrophilic pre-treatment. The hydrophobic and hydrophilic treatments were carried out in the same manner as in Example 9.

The thickness of the blackhead removing layer was 0.14 mm (thickness of the layer when dried), and the thickness of the part where the base layer and blackhead removing layer are overlapped was about 20% of the thickness of the base layer.

Example 11

A blackhead removing sheet was prepared in the same manner as in Example 8 except that one side (surface 51) of the base layer was subjected to a hydrophobic pre-treatment, while the other side (laminating surface 52) was subjected to a hydrophilic pre-treatment. The hydrophobic and hydrophilic treatments were carried out in the same manner as in Example 9.

The thickness of the blackhead removing layer was 0.14 mm (thickness of the layer when dried), and the thickness of the part where the base layer and blackhead removing layer are overlapped was about 20% of the thickness of the base layer Example 12

A blackhead removing sheet was prepared in the same manner as in Example 11 except that the composition of the blackhead removing agent was as shown in Table 3.

The thickness of the blackhead removing layer was 0.2 mm (thickness of the layer when dried), and the thickness of the part where the base layer and blackhead removing layer are overlapped was about 45% of the thickness of the base layer.

Example 13

A blackhead removing sheet was prepared in the same manner as in Example 11 except that the composition of the blackhead removing agent was as shown in Table 3.

The thickness of the blackhead removing layer was 0.25 mm (thickness of the layer when dried), and the thickness of the part where the base layer and blackhead removing layer are overlapped was about 20% of the thickness of the base layer.

Comparative Example 1

A blackhead removing sheet was prepared in the same manner as in Example 1 except that the amount of the glycerin serving as the plasticizer that was compatible with the water-soluble macromolecular compound was changed to 2 parts by weight.

Comparative Example 2

A blackhead removing sheet was prepared in the same manner as in Comparative Example 1 except that 1 parts by weight of titanium dioxide was added as filler and that the amount of the plasticizer that was compatible with the water-soluble macromolecular compound was also changed.

Comparative Example 3

A blackhead removing sheet was prepared in the same manner as in Comparative Example 1 except that 100 parts by weight of polyvinyl alcohol was used as the water-soluble macromolecular compound and that the amount of the 1,3-butanediol serving as the plasticizer that was compatible with the water-soluble macromolecular compound was changed to 1 part by weight.

Comparative Example 4

A blackhead removing sheet was prepared in the same manner as in Example 6 except that a nonwoven fabric consisting of polyester fibers (fineness: 1.0 denier; basis weight: 60 g/m$^2$; thickness: 0.5 mm) was used as the base layer.

The thickness of the blackhead removing layer was 0.15 mm (thickness of the layer when dried), and the thickness of the part where the base layer and blackhead removing layer are overlapped was about 70% of the thickness of the base layer.

Comparative Example 5

The blackhead removing sheet of the comparative example was prepared in the same manner as in Comparative Example 4 except that a nonwoven fabric consisting of polypropylene fibers (fineness: 2.5 denier; basis weight: 40 g/m$^2$; thickness: 0.5 mm) was used as the base layer.

The thickness of the blackhead removing layer was 0.14 mm (thickness of the layer when dried), and the thickness of the part where the base layer and blackhead removing layer are overlapped was about 75% of the thickness of the base layer.

Comparative Example 6

The blackhead removing sheet of the comparative example was prepared in the same manner as in Comparative Example 4 except that a nonwoven fabric consisting of polyester fibers (fineness: 5.2 denier; basis weight: 80 g/m$^2$; thickness: 0.7 mm) was used as the base layer.

The thickness of the blackhead removing layer was 0.14 mm (thickness of the layer when dried), and the thickness of the part where the base layer and blackhead removing layer are overlapped was about 85% of the thickness of the base layer.

2. Assessment of Blackhead Removing Capabilities

The blackhead removing capabilities of the blackhead removing sheet prepared in Examples 1 through 13 and Comparative Examples 1 through 6 were assessed.

First, ten panelists wet the area around the nose with a suitable amount of water (distilled water), and applied the blackhead removing sheets prepared in Examples 1 through 13 and Comparative Examples 1 through 6. The sheets were allowed to stand for 10 to 12 minutes, and the blackhead removing sheets were then peeled off.

The initial adhesion of the blackhead removing sheet (adhesion to skin surface), drying properties, anti-permeability (index of whether or not the blackhead removing agent was exuded through the surface of the base layer), blackhead removing properties, ease of peeling (whether or not any blackhead removing agent was left on the skin), and irritation at peeling were assessed in this test. These parameters were assessed by 5 ranks based on the following criteria. The results of the assessment are summarized in Table 5.

5: excellent
4: good
3: fair
2: poor
1: extremely poor

As shown in Table 5, since the blackhead removing sheets of the Examples all had excellent drying properties, they were dried sufficiently to allow blackheads to be removed 10 to 12 minutes after application. Better blackhead removing capabilities could thus be brought about more rapidly after application. Furthermore, the blackhead removing sheets could be peeled off without leaving any blackhead removing agent on the surface of the skin.

It has also been seen that the blackhead removing sheets of the Examples had better initial application and good adhesion to the skin. It has additionally been seen that the blackhead removing sheets of the Examples resulted in very low irritation of the skin when the blackhead removing sheets were peeled off from the skin. Furthermore, in the blackhead removing agent of the blackhead removing sheets of the Examples, it was not found to exude from the surface of the base layer.

In contrast, the blackhead removing layers of the blackhead removing sheets in Comparative Examples 1 through 3 did not dry sufficiently in 10 to 12 minutes, and blackheads could not be satisfactorily removed. These results showed that the blackhead removing sheets of Comparative Examples 1 through 3 were inferior in terms of drying properties and blackhead removing capabilities. Because the blackhead removing sheets in Comparative Examples 1 through 3 did not dry sufficiently, some of the blackhead removing agent was left on the skin when the blackhead removing sheets were peeled off of the skin. These results showed that the blackhead removing sheets of Comparative Examples 1 through 3 was inferior in terms of ease of peeling.

The blackhead removing sheets in Comparative Examples 4 through 6 did not adhere to the skin in some places when applied to the skin. These results showed that the blackhead removing sheets of Comparative Examples 4 through 6 were inferior in terms of conformability to the curved surface and blackhead removing capabilities.

The blackhead removing sheets in Comparative Examples 4 through 6 also suffered from poor handling due to stickiness caused by penetration of the blackhead removing agent as a result of the high proportion of the thickness of the parts where the base layer and blackhead removing layer are overlapped relative to the thickness of the base layer, and they also left residue on the skin.

3. Measurement of Loss on Drying

The loss on drying was determined for the blackhead removing sheets prepared in Examples 1 through 13 and Comparative Examples 1 through 6.

To determine the loss on drying, blackhead removing sheets which had each been adjusted to a predetermined size were first weighed ($W_A$). They were then dried for 180 minutes at 110° C. and subsequently weighed again ($W_B$). The loss on drying was determined on the basis of Equation (1).

$$\text{Loss on drying } (\%) = \{(W_A - W_B)/W_A\} \times 100 \quad (1)$$

$W_A$: weight of blackhead removing sheet before drying [g]

$W_B$: weight of blackhead removing sheet after drying [g]

Tables 1 through 4 show the loss on drying for each of the blackhead removing sheets.

The results in Tables 1 through 4 show the following. Since the blackhead removing sheets in the Examples all contained suitable amounts of solvent, they can exhibit good flexibility and conformability to curved surface of the blackhead removing sheets, even without containing a plasticizer that was compatible with the water-soluble macromolecular compound. The blackhead removing sheets in the Examples also had excellent good blackhead removing capabilities. The blackhead removing sheets in the Examples also had less irritation on the skin when the blackhead removing sheet were peeled off of the skin.

When the blackhead removing agents prepared in the Examples were used in the form of peel-off types of blackhead removing agents, they had the same good drying properties and blackhead removing properties as those in the aforementioned Examples. There was also virtually no irritation of the skin, with no blackhead removing agent left over on the skin when peeled off.

According to the blackhead removing agent and blackhead removing sheet of the present invention, the blackhead removing sheet dries rapidly after being spread on or applied to the skin surface. Therefore, they can remove blackheads more rapidly.

Furthermore, according to the blackhead removing agent and blackhead removing sheet of the present invention, the blackhead removing sheet has good spreadability, skin conformability, adhesion, and sticking properties when spread or applied. Therefore, it is possible to remove blackheads more effectively.

Additionally, according to the blackhead removing agent and blackhead removing sheet of the present invention, it is possible to prevent parts of the blackhead removing agent (blackhead removing layer) from being left on the skin when the blackhead removing sheet is peeled off from the skin. The blackhead removing sheet also can be peeled off without overly irritating the skin. In other words, the blackhead removing sheet can be peeled off from the skin without injuring the skin.

According to the blackhead removing sheet of the present invention, the base layer contained in the blackhead removing sheet is composed of a specific nonwoven fabric. This makes it possible to provide a blackhead removing sheet with better conformability to skin texture and curves, and better adhesion on the skin. Such a blackhead removing sheet can exhibit better blackhead removing capabilities.

According to the blackhead removing sheet of the present invention, excessive overlapping of the base layer and blackhead removing layer can be controlled. Therefore, it is possible to prevent the blackhead removing agent from being exuded from the surface of the base layer, thus enabling to provide a blackhead removing sheet with better handling properties.

According to the blackhead removing sheet of the present invention, it is possible to form a blackhead removing layer with better blackhead removing properties by using lower amounts of a blackhead removing agent. Therefore, it is possible to shorten the time needed to dry the blackhead removing sheet, and to remove blackheads more efficiently.

Finally, the method for manufacturing the blackhead removing sheet of the present invention allows a blackhead removing sheet having the aforementioned effects to be easily manufactured.

TABLE 1

| Composition of Blackhead Removing Agent [parts by weight] | | | | | |
|---|---|---|---|---|---|
| | Example 1 | Example 2 | Example 3 | Example 4 | Example 5 |
| Water-soluble marcromolecular | | | | | |
| P(VP-VAc)* Copolymerization ratio of 6:4 (weight-average molecular weight; about 40,000) | 100 (75.14) | 100 (69.41) | 100 (68.65) | — | 100 (50.25) |
| P(VP-VAc) Copolymerization ratio of 7:3 (weight-average molecular weight; about 50,000) | — | — | — | 100 (75.95) | — |
| Polyvinyl alcohols | — | 10(6.94) | — | — | — |
| Polyvinyl acetate | — | — | 10(6.86) | — | — |
| Filler | | | | | |
| Silica (mean particle diameter: 5 μm) | 20(15.03) | 20(13.88) | 20(13.73) | 20(15.19) | 80(40.20) |
| Titanium dioxide (mean particle diameter: 1 μm) | 1(0.75) | 1(0.69) | 1(0.69) | 1(0.76) | 1(0.50) |
| Plasticizer | | | | | |
| Glycerin | — | — | — | — | — |
| 1,3-butanediol | — | — | — | — | — |
| Solvent | | | | | |
| Water | 50(4.5) | 50(4.5) | 50(5.0) | 50(4.0) | 75(4.5) |
| Ethanol | 50(4.5) | 50(4.5) | 50(5.0) | 50(4.0) | 75(4.5) |

TABLE 1-continued

| Composition of Blackhead Removing Agent [parts by weight] | | | | | |
|---|---|---|---|---|---|
| | Example 1 | Example 2 | Example 3 | Example 4 | Example 5 |
| Additives | | | | | |
| Preservative | 0.1(0.075) | 0.1(0.069) | 0.1(0.069) | 0.1(0.076) | 0.1(0.050) |
| Thickness of Blackhead Removing Layer [mm] | 0.17 | 0.15 | 0.17 | 0.16 | 0.16 |
| Loss on Drying [%] | 9 | 8 | 10 | 8 | 9 |
| Proportion of Overlapped Part with respect to Thickness of Base Layer [%] | 20 | 18 | 18 | 25 | 20 |

The numbers given in parentheses designates the content of the component in the blackhead removing layer.
P(VP-VAc): copolymers of N-vinyl-2-pyrrolidone and vinyl acetate

TABLE 2

| Composition of Blackhead Removing Agent [parts by weight] | | | | |
|---|---|---|---|---|
| | Example 6 | Example 7 | Example 8 | Example 9 |
| Water-soluble marcromolecular | | | | |
| P(VP-VAc) Copolymerization ratio of 6:4 (weight-average molecular weight; about 40,000) | 100 (69.44) | 100 (72.98) | — | 100 (69.44) |
| P(VP-VAc) Copolymerization ratio of 7:3 (weight-average molecular weight; about 50,000) | — | — | 100 (69.12) | — |
| Polyvinyl alcohols | — | 10(3.65) | 5(3.46) | — |
| Polyvinyl acetate | — | — | 5(3.46) | — |
| Polyacrylic acid (average molecular weight about 100,000) | — | — | — | — |
| Polyvinyl pyrrolidone (average molecular weight about 200,000) | 10(6.94) | — | — | — |
| Filler | | | | |
| Silica (mean particle diameter: 5 μm) | 20(13.89) | 20(14.60) | 20(13.82) | 20(13.89) |
| Titanium dioxide (mean particle diameter: 1 μm) | 1(0.69) | 1(0.73) | 1(0.69) | 1(0.69) |
| Plasticizer | | | | |
| Glycerin | — | 0.001 (0.00073) | — | — |
| 1,3-butanediol | — | 0.001 (0.00073) | — | — |
| Squalane (oil components) | — | — | — | — |
| Polyoxyethlene hydrogenated caster oil (surfactants) | — | — | — | — |

TABLE 2-continued

Composition of Blackhead Removing Agent [parts by weight]

| | Example 6 | Example 7 | Example 8 | Example 9 |
|---|---|---|---|---|
| Solvent | | | | |
| Water | 50(4.5) | 50(4.0) | 50(5.0) | 50(4.0) |
| Ethanol | 50(4.5) | 50(4.0) | 50(5.0) | 50(4.0) |
| Additives | | | | |
| Preservative | 0.05 (0.035) | 0.05 (0.036) | 0.05 (0.035) | 0.05 (0.035) |
| Thickness of Blackhead Removing Layer [mm] | 0.15 | 0.14 | 0.14 | 0.15 |
| Loss on Drying [%] | 9 | 8 | 9 | 9 |
| Proportion of Overlapped Part with respect to Thickness of Base Layer [%] | 20 | 30 | 20 | 25 |

The numbers given in parentheses designates the content of the component in the blackhead removing layer.

TABLE 3

Composition of Blackhead Removing Agent [parts by weight]

| | Example 10 | Example 11 | Example 12 | Example 13 |
|---|---|---|---|---|
| Water-soluble marcromolecular | | | | |
| P(VP-VAc) Copolymerization ratio of 6:4 (weight-average molecular weight; about 40,000) | 100(72.98) | — | — | — |
| P(VP-VAc) Copolymerization ratio of 7:3 (weight-average molecular weight; about 50,000) | — | 100(69.12) | — | — |
| Polyvinyl alcohols | 10(3.65) | 5(3.46) | — | 100(64.52) |
| Polyvinyl acetate | — | 5(3.46) | — | — |
| Polyacrylic acid (aveage molecular weight; about 100,000) | — | — | 100(75.17) | — |
| Polyvinyl pyrrolidone (average molecular weight; about 200,000) | — | — | — | 20(12.90) |
| Filler | | | | |
| Silica (mean particle diameter: 5 μm) | 20(14.60) | 20(13.82) | 20(15.03) | 20(12.90) |
| Titanium dioxide (mean particle diameter: 1 μm) | 1(0.73) | 1(0.69) | 1(0.75) | 1(0.65) |
| Plasticizer | | | | |
| Glycerin | 0.001 (0.00073) | — | — | — |
| 1,3-butanediol | 0.001 (0.00073) | — | 0.001 (0.00073) | — |
| Squalane (oil components) | — | 0.5(0.35) | — | — |
| Polyoxyethylene hydrogenated caster oil (surfactants) | — | 0.1(0.069) | — | — |
| Solvent | | | | |
| Water | 50(4.0) | 50(4.5) | 50(4.5) | 50(4.5) |
| Ethanol | 50(4.0) | 50(4.5) | 50(4.5) | 50(4.5) |
| Additives | | | | |
| Preservative | 0.05(0.036) | 0.05(0.035) | 0.05(0.038) | 0.05(0.032) |
| Thickness of Blackhead Removing Layer [mm] | 0.14 | 0.14 | 0.20 | 0.25 |
| Loss on Drying [%] | 8 | 9 | 9 | 9 |
| Proportion of Overlapped Part with respect to Thickness of Base Layer [%] | 20 | 20 | 45 | 20 |

The numbers given in parentheses designates the content of the component in the blackhead removing layer.

TABLE 4

Composition of Blackhead Removing Agent [parts by weight]

|  |  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|
| Water-soluble macromolecular | P(VP-VAc) Copolymerization ratio of 6:4 (weight-average molecular weight: about 40,000) | 100(73.11) | 100(89.13) | — | 100(69.44) | 100(72.98) | — |
|  | P(VP-VAc) Copolymerization ratio of 7:3 (weight-average molecular weight: about 50,000) | — | — | — | — | — | 100(69.12) |
|  | Polyvinyl alcohols | — | — | 100(75.35) | — | 10(3.65) | 5(3.46) |
|  | Polyvinyl acetate | — | — | 5(3.46) | — | — | 5(3.46) |
|  | Polyacrylic acid (average molecular weight: about 100,000) | — | — | — | — | — | — |
|  | Polyvinyl pyrrolidone (average molecular weight: anout 200,000) | — | — | — | 10(6.94) | — | — |
| Filler | Silica (mean particle diameter: 5 μm) | 20(14.62) | — | 20(15.07) | 20(13.89) | 20(14.60) | 20(13.82) |
|  | Titanium dioxide (mean particle diameter: 1 μm) | 1(0.73) | 1(0.89) | 1(0.75) | 1(0.69) | 1(0.73) | 1(0.69) |
| Plasticizer | Glycerin | 2(1.46) | 1(0.89) | — | — | 0.001 (0.00073) | — |
|  | 1,3-butanediol | — | — | 1(0.75) | — | 0.001 (0.00073) | — |
| Squalane(oil components) |  | — | — | — | — | — | 0.5(0.35) |
| Polyoxyethylene hydrogenated castor oil (surfactants) |  | — | — | — | — | — | 0.1(0.069) |
| Solvent | Water | 50(5.0) | 50(4.5) | 50(4.0) | 50(4.5) | 50(4.0) | 50(4.5) |
|  | Ethanol | 50(5.0) | 50(4.5) | 50(4.0) | 50(4.5) | 50(4.0) | 50(4.5) |
| Additives | preservatives | 0.1 (0.073) | 0.1 (0.089) | 0.1 (0.075) | 0.05 (0.035) | 0.05 (0.036) | 0.05 (0.035) |
| Thickness of Blackhead Removing Layer[mm] |  | 0.17 | 0.15 | 0.16 | 0.15 | 0.14 | 0.14 |
| Loss on Drying[%] |  | 10 | 9 | 8 | 9 | 8 | 9 |
| Proportion of Overlapped Part with respect to Thickness of Base Layer[%] |  | 25 | 28 | 22 | 70 | 75 | 85 |

The numbers given in parentheses designates the content of the component in the blackhead removing layer.

TABLE 5

Results of Assessment for Blackhead Removing Capabilities

[average rank]

|  | Initial Adhesion | Drying Property | Anti-Permeability | Blackhead Removing Property | Ease of Peeling | Irritation at peeling |
|---|---|---|---|---|---|---|
| Example 1 | 4.6 | 5.0 | 4.6 | 4.6 | 4.0 | 4.1 |
| Example 2 | 4.2 | 4.5 | 4.8 | 4.0 | 4.8 | 4.5 |
| Example 3 | 4.2 | 4.6 | 4.8 | 4.1 | 4.5 | 4.4 |
| Example 4 | 4.6 | 5.0 | 4.6 | 4.5 | 4.1 | 4.2 |
| Example 5 | 4.3 | 5.0 | 5.0 | 4.4 | 4.2 | 4.3 |
| Example 6 | 4.6 | 5.0 | 5.0 | 4.6 | 4.0 | 4.1 |
| Example 7 | 4.4 | 4.8 | 4.8 | 4.6 | 4.1 | 4.2 |
| Example 8 | 4.2 | 4.8 | 4.9 | 4.5 | 4.0 | 4.1 |
| Example 9 | 4.6 | 5.0 | 5.0 | 4.8 | 4.0 | 4.1 |
| Example 10 | 4.4 | 4.8 | 5.0 | 4.8 | 4.0 | 4.2 |
| Example 11 | 4.3 | 4.8 | 5.0 | 4.7 | 4.1 | 4.1 |
| Example 12 | 4.2 | 4.5 | 4.8 | 4.2 | 4.2 | 4.2 |
| Example 13 | 4.3 | 4.6 | 4.9 | 4.4 | 4.3 | 4.1 |
| Comp.Ex. 1 | 4.5 | 2.6 | 4.0 | 3.5 | 3.7 | 4.1 |
| Comp.Ex. 2 | 4.2 | 2.5 | 3.4 | 3.3 | 3.9 | 4.0 |
| Comp.Ex. 3 | 2.8 | 2.4 | 3.8 | 2.8 | 3.9 | 4.0 |
| Comp.Ex. 4 | 3.1 | 4.5 | 3.5 | 3.4 | 3.8 | 3.6 |
| Comp.Ex. 5 | 2.8 | 4.0 | 2.3 | 3.1 | 3.2 | 3.0 |
| Comp.Ex. 6 | 2.3 | 4.0 | 2.8 | 2.8 | 3.3 | 3.1 |

What is claimed:

1. A blackhead removing sheet comprising:
   a a base layer composed of a nonwoven fabric having a fineness of at least 0.0001 denier but less than 0.1 denier, the base layer having a thickness of 0.05 to 1 mm; and
   b a blackhead removing layer provided on the base layer, the blackhead removing layer including a blackhead removing agent that contains a water-soluble macromolecular compound as a primary component thereof, the blackhead removing agent comprising a filler and a plasticizer that is compatible with the water-soluble macromolecular compound, in which the amount of the plasticizer in the blackhead removing agent is less than 0.01 parts by weight with respect to 100 parts by weight of the water-soluble macromolecular compound and wherein the blackhead removing layer is partly impregnated in the base layer with the thickness of the part where the base layer and the blackhead removing layer overlap is from 1 to 65% of the thickness of the base layer.

2. The blackhead removing sheet of claim 1 wherein the basis weight of the base layer is 20 to 200 g/m$^2$.

3. The blackhead removing sheet of claim 1 wherein a hydrophilic treatment is carried out on at least one surface of the base layer.

4. The blackhead removing sheet of claim 1 wherein a hydrophobic treatment is carried out on at least one surface of the base layer.

5. The blackhead removing sheet of claim 1 wherein said blackhead removing agent further comprises:
   a. a filler selected from the group consisting of inorganic fillers, organic fillers, and mixtures thereof; and
   b. a polyhydric alcohol plasticizer that is compatible with the water-soluble macromolecular compound, in which the amount of the plasticizer in the blackhead removing agent is less than 0.01 parts by weight with respect to 100 parts by weight of the water-soluble macromolecular compound.

6. The blackhead removing sheet of claim 5 wherein the plasticizer has a boiling point of 120 C. or higher at ordinary pressure.

7. The blackhead removing sheet of claim 5 wherein the water-soluble macromolecular compound includes a copolymer of N-vinyl-2-pyrrolidone and vinyl acetate as a primary component thereof.

8. The blackhead removing sheet of claim 7 wherein the copolymerization ratio of the copolymer of N-vinyl-2-pyrrolidone and vinyl acetate is within the range of 5:95 to 95:5.

9. The blackhead removing sheet of claim 5 wherein the weight-average molecular weight of the water-soluble macromolecular compound is 10,000 to 3,000,000.

10. The blackhead removing sheet of claim 5 wherein the amount of the filler is less than 120 parts by weight with respect to 100 parts by weight of the water-soluble macromolecular compound.

11. The blackhead removing sheet of claim 5 wherein the mean particle diameter of the filler is within the range of 5 nm to 50 $\mu$m.

12. The blackhead removing sheet of claim 5 wherein the blackhead removing agent contains an inorganic filler as a primary component thereof.

13. The blackhead removing sheet of claim 5 wherein the blackhead removing agent contains water and/or a C1 to C4 monohydric alcohol as a solvent therefor.

14. The blackhead removing sheet of claim 5 wherein a loss on drying is 3 to 30%.

15. The blackhead removing sheet of claim 1 wherein the nonwoven fabric has a fineness in the range from 0.0003 denier to 0.07 denier.

16. The blackhead removing sheet of claim 1 wherein the nonwoven fabric has a fineness in the range from 0.0005 denier to 0.04 denier.

* * * * *